United States Patent
Klein et al.

(10) Patent No.: US 10,299,776 B2
(45) Date of Patent: May 28, 2019

(54) BIODEGRADABLE APPARATUS AND METHOD FOR CLOSURE OF TROCAR DEFECTS

(71) Applicants: Michael Sigmund Klein, Salinas, CA (US); Michael George Fourkas, Sunnyvale, CA (US); Widya Mulyasasmita, Mountain View, CA (US); James Su, Santa Clara, CA (US)

(72) Inventors: Michael Sigmund Klein, Salinas, CA (US); Michael George Fourkas, Sunnyvale, CA (US); Widya Mulyasasmita, Mountain View, CA (US); James Su, Santa Clara, CA (US)

(73) Assignee: LAP IQ, Inc, Los Altos, CA (US)

( * ) Notice: Subject to any disclaimer, the term of this patent is extended or adjusted under 35 U.S.C. 154(b) by 200 days.

(21) Appl. No.: 15/256,728

(22) Filed: Sep. 5, 2016

(65) Prior Publication Data

US 2017/0100111 A1    Apr. 13, 2017

Related U.S. Application Data

(63) Continuation-in-part of application No. 12/758,027, filed on Apr. 11, 2010, now Pat. No. 8,506,593, and a continuation-in-part of application No. 13/475,996, filed on May 20, 2012, now Pat. No. 9,011,485, and a continuation-in-part of application No. 14/210,230, (Continued)

(51) Int. Cl.
*A61B 17/00* (2006.01)
*A61B 17/10* (2006.01)
*A61B 34/30* (2016.01)

(52) U.S. Cl.
CPC .......... *A61B 17/0057* (2013.01); *A61B 17/10* (2013.01); *A61B 34/30* (2016.02); *A61B 2017/00004* (2013.01); *A61B 2017/00606* (2013.01); *A61B 2017/00623* (2013.01); *A61B 2017/00637* (2013.01);
(Continued)

(58) Field of Classification Search
CPC ........ A61B 17/0057; A61B 2017/0057; A61B 2017/00575; A61B 2017/00606; A61B 2017/00615; A61B 2017/00637; A61B 17/688; A61B 17/08; A61B 17/10
USPC ....... 606/153, 154, 157, 158, 213, 215, 301, 606/306, 315–317, 324; 623/23.72
See application file for complete search history.

(56) References Cited

U.S. PATENT DOCUMENTS 5,342,393 A * 8/1994 Stack ................. A61B 17/0057
                                                                    24/453
5,366,460 A   11/1994 Eberbach
(Continued)

OTHER PUBLICATIONS

Maurus, P.B. and Kaeding, C.C., "Bioabsorbable Implant Material Review", Oper. Tech. Sports Med 12, 158-160, 2004.
(Continued)

*Primary Examiner* — Thomas M McEvoy
(74) *Attorney, Agent, or Firm* — Michael Toback

(57) ABSTRACT

A method for maintaining the alignment of the edges of a trocar defect by inserting into a defect a device for compressing the tissue such that part of the device is above while the other is below the defect, then pulling back on the device so that the part below the defect is up against the defect, then while holding the device below the defect in place, push down on the part above the wound so that it compresses the tissue. Finally, release the device from the insertion tool.

7 Claims, 13 Drawing Sheets

Related U.S. Application Data filed on Mar. 13, 2014, now Pat. No. 9,456,819, and a continuation of application No. 62/215,715, filed on Sep. 8, 2015.

(52) U.S. Cl.
CPC .............. *A61B 2017/00646* (2013.01); *A61B 2017/00654* (2013.01); *A61B 2017/00659* (2013.01)

(56) References Cited

U.S. PATENT DOCUMENTS

| | | | |
|---|---|---|---|
| 6,120,539 | A | 9/2000 | Eldridge |
| 6,241,768 | B1 | 6/2001 | Agarwal |
| 2002/0004661 | A1* | 1/2002 | Sevrain ................ A61B 17/688 606/324 |
| 2003/0181988 | A1 | 9/2003 | Rousseau |
| 2006/0015142 | A1 | 1/2006 | Malazgirt |
| 2006/0282105 | A1 | 12/2006 | Ford |

OTHER PUBLICATIONS

Middleton, J. and Tipton A. "Synthetic Biodegradable Polymers As Medical Devices" Medical Plastics and Biomaterials Magazine, Mar. 1998.

Gilding, D.K. and Reed, A.M. "Biodegradable Polymers for Use in Surgery," Polymer, 20, 1459-1464 (Dec. 1979).

"Plastic That Comes Alive: Biodegradable plastic scaffolds support living cells in three dimensional matrices so they can grow together into tissues and even whole organs" by.

Astete, C.E. and Sabliov, C.M., "Synthesis and Characterization of PLGA Nanoparticles", Journal of Biomaterials Science Polymer Edition 17 (3) 247-289 (2006).

* cited by examiner

BIODEGRADABLE APPARATUS AND METHOD FOR CLOSURE OF TROCAR DEFECTS

This patent is a continuation of "Biodegradable Apparatus and Method for Closure of Trocar Defects", filed on Mar. 13, 2014 as U.S. application Ser. No. 14/210,230. This patent is also a continuation in part of "An Implatable Biodegradable Wound Closure Device and Method", filed on Apr. 11, 2010 as U.S. application Ser. No. 12/758,027 and issued as U.S. Pat. No. 8,506,593 on Aug. 13, 2013. This patent is also a continuation in part of "Implantable Biodegradable Would Closure Device and Method", filed on May 20, 2012 as U.S. application Ser. No. 13/475,996 and issued as U.S. Pat. No. 9,011,485 on Apr. 21, 2015. It is also a continuation of "Implantable Tissue Scaffold and Method", filed on Mar. 14, 2013 as U.S. Application No. 61/786,276.

BACKGROUND OF THE INVENTION

Field of the Invention

The present invention generally relates to a trocar defect closure device that is used either directly by a surgical team or indirectly as an attachment to a robotics controller to repair the defect typically left in the fascia layer during laparoscopic surgery by an instrument called a trocar.

Laparoscopic surgery was introduced as an alternative to open surgical methods. Also referred to as minimally invasive surgery, the technique allows for small incision access to the intra-abdominal cavity. The approach utilizes specialized equipment for the purposes of inflating the abdominal cavity with gas, deploying and exchanging instruments during the operation, and real time imaging with a videoscopic camera. Single port and robotic surgical procedures were developed from and utilize minimally invasive technologies.

A laparoscopic trocar is a surgical device used in laparoscopic procedures to pierce and access the wall of an anatomical cavity, thereby forming a passageway providing communication with the inside of the cavity. Other medical instruments such as videoscopes and operating instruments can thereafter be inserted through the passageway to perform various surgical procedures within the abdominal cavity. Multiple trocars are often used to accommodate a variety of specialized surgical instruments. Laparoscopic trocars are typically 5-15 mm in diameter.

When the procedures are over, the laparoscopic trocars are removed, leaving residual defects in the fascia-peritoneal layer. If trocar port defects are not repaired, there is risk of trocar site herniation (TSH). The incidence of post-operative TSH increases with use of larger trocar port sizes. The trocar site defect is located deep in the abdominal wall, making it difficult to view and for the surgeon to repair reliably.

Trocar site herniation (TSH) is a recognized complication of incomplete surgical repair. Symptoms are varied, but are frequently localized in nature. Major complications include omental and intestinal herniation, with incarceration and bowel obstruction. Fascial closure of any trocar insertion site larger than 5 mm has now been established and is routinely practiced worldwide.

However, the closure of such a trocar site fascial defect using the conventional suturing technique is often technically difficult, time consuming and frequently ineffective. Working in the port tissue tunnel is dangerous due to the narrow size of skin incision, thickness of the subcutaneous fatty layer, and recessed trocar port fascial defect. Moreover, blind suturing after the abdomen has been decompressed is dangerous.

Problems arise when both sides of the defect are not approximated or sutured. In overweight and (high Body Mass Index) obese patients with thick abdominal walls, reliable fascia closure is particularly difficult to achieve. This results in a higher TSH formation rate and associated complications, such as a bowel incarceration. Surgical literature reports an overall 6% trocar port herniation rate. Patients requiring, re-operation, re-hospitalization, and extended disability, experience significant economic loss.

A number of techniques and devices were designed to enable secure closure of the fascial layer defect. These are based on approaches in which suture is positioned on either side of the trocar defect, enabling tying and ligating suture by hand. For this purpose either a tapered suture or a variety of straight needles through which sutures are grabbed or clasped have been used. The Carter-Thomason or Riza-Ribe® needles have positioned a mechanical catch at the end of their needle assembly for grabbing the closure suture. An automated port closure suturing device is also available.

Although promoted as easy and quick methods, the needle based closure methods require several tedious steps involving frequent re-positioning of the camera, visualization of the needles during their entrance into the peritoneal cavity, and feeding of the graspers or suture passers with ends of sutures. All of these maneuvers have to be repeated in sequence for every trocar defect closed. Needle directed suturing techniques are time and effort consuming, even in the best of hands.

Needle based port closure methods were enhancements to the conventional method of port closure because tight working spaces were difficult to navigate with standard sutures. Moreover, a series of traumatic manipulations were often required when applying conventional sutures. These measures frequently include forceful pushing, pulling and retraction of the wound to achieve maximum exposure of the fascial defect. As manipulation of the wound increases, inflammation and risk of ensuing infection rise considerably. Edema and the collection of seroma or hematoma, predispose to wound dehiscence and trocar site hernia (TSH.)

To summarize, excessive manipulation of tissue frequently occur when conventional suturing techniques are used. Trauma undermines the "minimally invasive" advantages otherwise realizable with laparoscopic surgery. Patients are subject to post-operative incisional pain and other complications at their trocar sites. Suturing creates excessive tension at the wound site, increasing the risk of the wound pulling apart. Excessive pressure tension forces are among the most common cause of wound breakdown.

Intra-corporeal suturing techniques are used infrequently to close trocar port defects under direct vision from within the abdominal cavity. Instead, most trocar ports are dosed from the outside, with the abdominal wall in a flattened configuration. As a result, the residual defect within the fascial layer is poorly visualized by the surgeon.

No matter which suturing technique or needle is used, it is not possible to eliminate the risk of trocar site hernias complications. As described in Malazgirt (US Patent Application, pub #20060015142 published Jan. 19, 2006), the current incidence is reportedly between 0.77-3%. The reported rates of hernia show that there is no superior method in the safe closure of the trocar fascial defect. As complex laparoscopic surgery becomes more common, the incidence of this complication increases.

Eldridge and Titone (U.S. Pat. No. 6,120,539 Issued Sep. 19, 2000) proposed a prosthetic repair fabric constructed from a combination of non-absorbable tissue-infiltratable fabric which faces the anterior surface of the fascia and an adhesion-resistant barrier which faces outward from the fascia. This prosthetic requires the use of sutures to hold it in place.

Eberbach (U.S. Pat. No. 5,366,460 Issued Nov. 22, 1994) proposed the use of a non-biodegradable fabric-coated loop inserted through the defect into the fascia wall, pressing against the posterior fascia wall from the intra-abdominal pressure.

Agarwal et al (U.S. Pat. No. 6,241,768 Issued Jun. 5, 2001) proposed a prosthetic device made of a biocompatible non-biodegradable mesh, which sits across the fascia defect using the abdominal pressure to hold it in place.

Rousseau (Pat Pub #20030181988) proposed a plug made of biocompatible non-biodegradable material which covers the anterior side of the fascia, the defect, as well as the posterior side of the fascia.

Malazgirt (Pat Pub #20060015142) proposed a plug/mesh non-biodegradable combination for repair of large trocar wounds. It is stated that it requires at least a "clean flat area around with a radius of 2.5 cm", and requires staples to hold it in place.

Ford and Torres (Pat Pub #20060282105) proposed a patch with a tether or strap, all made of non-biodegradable biocompatible material placed against the anterior wall of the fascia defect.

Sargeant et al (U.S. Pat. No. 8,617,206 Issued Dec. 31, 2013 proposed a biocompatible wound closure device with a plug member with a single tissue facing surface, where the plug is attached to an elongate body which goes through the trocar defect.

SUMMARY

A biodegradable device for providing scaffolding for a trocar defect to promote healing. The device consists of inner and outer scaffolding offset by a connector. The device is arranged so the distance between the lower surface of the outer scaffolding and upper surface of the inner scaffolding holds the device around the trocar defect while promoting tissue growth. The surfaces of the scaffolding in contact with the trocar defect are textured to maximize adherence to tissue.

BRIEF DESCRIPTION OF THE DRAWINGS

The aforementioned features and advantages of the invention as well as additional features and advantages thereof will be more clearly understandable after reading detailed descriptions of embodiments of the invention in conjunction with the following drawings.

DETAILED DESCRIPTION OF PREFERRED EMBODIMENTS

Figure 1:
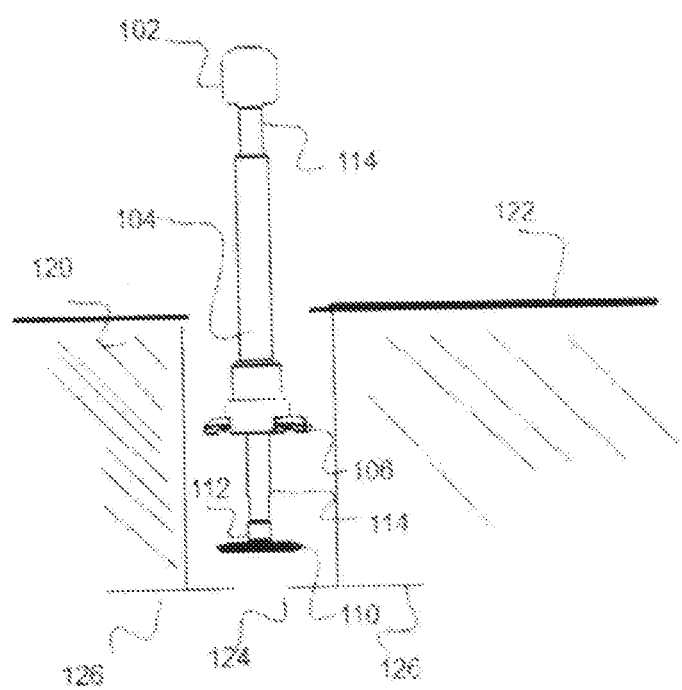
FIG. 1 shows one embodiment of the apparatus as it would appear on deployment in the trocar tunnel.

FIG. 1 shows views of one or more embodiments of the device configured to be implanted. In one or more embodiments, an applicator consists of a handle 102, inner applicator 114, outer applicator 104, coupling to outer scaffolding 106, and coupling to inner scaffolding 110. In one or more embodiments, the biodegradable scaffolding consists of an outer scaffolding 106, inner scaffolding 110, and coupling 112. The inner scaffolding 110 is meant to be inserted into the trocar defect and stays underneath the trocar defect once deployed. The inner scaffold 110 has a tissue facing surface that is meant to maintain contact with the lower surface of the tissue surrounding the trocar defect. The inner scaffold has a circular or elliptical cross section, such that it has a base diameter that is large enough to prevent it from extrusion through the trocar defect. In one or more embodiments, the base diameter varies with the size of the trocar defect being closed. The outer scaffolding 106 has a tissue facing surface that is meant to maintain contact with the upper surface of the tissue surrounding the trocar defect. The coupling 112 holds the two scaffolds in place so that the tissue stays in place, and while healing is encouraged to grow. In one or more embodiments the coupling 112 is ribbed to enable the device to be used with various thickness of tissue around the fascia defect. The outer scaffolding 106, coupling 112, and inner scaffolding 110 will be collectively referred to herein as the scaffold assembly. The mechanical properties of the scaffold both maintains alignment of the fascial planes of the defect during healing and provides a mechanical barrier to herniation during healing until the tissue is sufficiently healed to prevent herniation. The scaffold assembly bridges the trocar defect, and fascial edges are aligned to prevent extrusion of the scaffolding assembly, or prolapse of intra-abdominal structures such as bowel or omentum thru trocar defect. The support remains in place while the tissue heals then is resorbed once the tissue is sufficiently healed, the tissue then able to prevent egress without the need for additional support.

In one or more embodiments, the shape of the surface of the inner scaffolding and outer scaffolding may vary, where the base diameter of the inner scaffolding would be the largest distance across the center of the surface, and the major and minor diameters of the outer scaffolding would be the largest and smallest distance across its surface. In one or more embodiments each of the inner and outer scaffolding could be scalloped circles. In other embodiments the inner scaffolding could be elliptical in shape. In other embodiments the inner or outer scaffolding or both could be one or more ellipses in a petal-like formation. In other embodiments the inner or outer scaffolding could be triangular.

The fascia has different characteristics on the top and bottom. The tissue aligning with the inner scaffolding 110 is made of a fine cellophane-like material called the peritoneum, while the fascia contacting the outer scaffold 106 is primarily muscle and subcutaneous fat. The trocar defect in the fascia may be a slit or star formation, such that it has a defect diameter. The inner scaffolding 110 placed below the defect but larger than this diameter would not be easily extruded through the defect. For a slit defect configuration, the inner scaffold will extend well beyond the width of the slit, for a star defect configuration this would be expected to buttress and extend well beyond the fascial tissue flaps.

In one or more embodiments, the tissue facing surface of the inner scaffolding 110 contacting the peritoneum has a texture on it which acts to increase the friction between the peritoneum and scaffold to reduce or eliminate the possibility of extrusion. Smaller perforation sizes in the inner scaffolding 110 act to bend or fold the peritoneum into it, helping to keep the tissue in place during the healing process. Larger perforation sizes in the upper scaffold 106 allow the muscle and fat to protrude through it, both to encourage growth of the tissue above and around the implanted device and acting further to keep the scaffold in place.

In one or more embodiments the inner applicator 114 and outer applicator 104 are configured to be held by a user to implant and align the device. In other embodiments, the inner applicator 114 and outer applicator 104 are configured to be coupled with a robotic device to enable a user to remotely implant the device.

Figure 8:
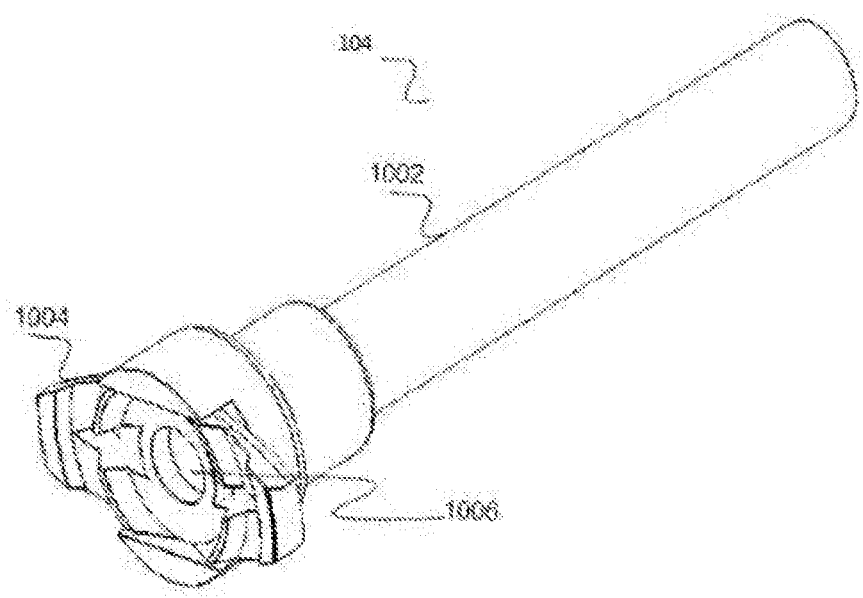
FIG. 8 shows a side view of the outer applicator
Figure 9:
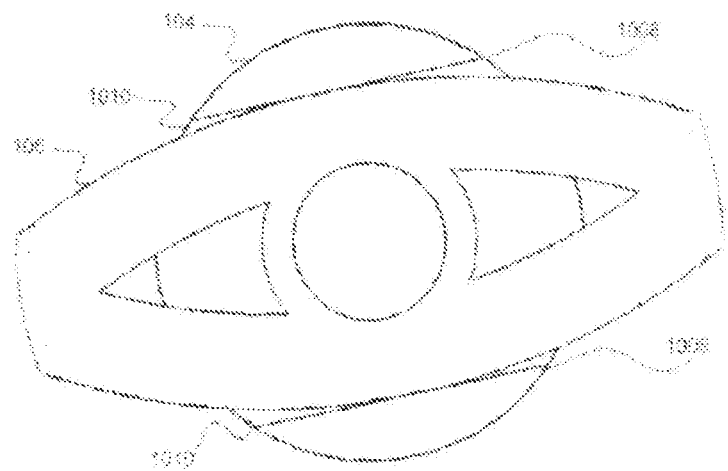
FIG. 9 shows a side view of the outer applicator with the biodegradable outer scaffolding in place.

In one or more embodiments the inner applicator 114 is connected to the biodegradable inner scaffold 110 by screwing into a threaded cylinder at its interior end, which is part of the biodegradable inner scaffold. In one or more embodiments, the inner applicator 114 slides inside the outer applicator 104 via a handle 102 attached to the inner applicator 114 at the exterior end. As shown in FIG. 8 and FIG. 9, the outer scaffolding 106 is secured to the interior end of the outer applicator 104 by and interference fit 1006.

Figure 2:
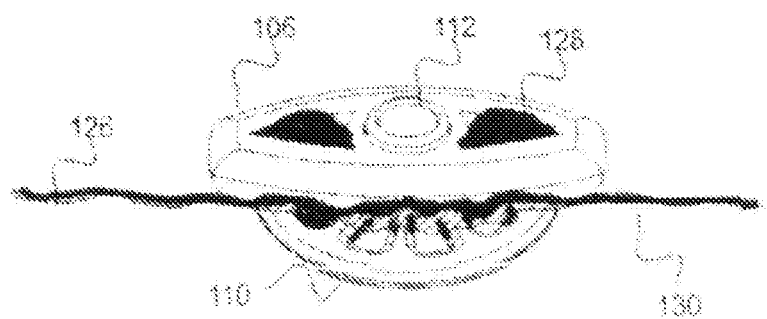
FIG. 2 shows the details of one embodiment of the coupling of the applicator to the scaffold inserted into a trocar defect and across the fascia planes of the wound.

FIG. 2 shows a detailed view of the coupling between the inner scaffolding 110, outer scaffolding 106 and fascia 126. In one or more embodiments, the inner scaffolding 110 is attached to the outer scaffolding 106 by a coupling 112 between the two. The scaffold assembly in place will have enough of a hold on the fascia 126 enough to hold it in place without injuring it. The outer scaffold 106 sits on top of the fascia 126. It is not necessary for the scaffold assembly to cover the entire defect. Rather, it serves the purpose of stabilizing the tissue and the edges of the defect anatomically aligned and co-apted to facilitate reliable wound healing.

The scaffold assembly is kept in place to hold, but not overly compress, the fascia 126 surrounding the trocar defect 216 to promote the healing process. In this figure, the inner scaffolding 110 is shown to be smaller than the outer scaffolding 106. In one or more embodiments, the purpose of the inner scaffolding is to stabilize the scaffold assembly to the defect, and so it must be at least wider than the width of the trocar defect separation, and wide enough to be able to couple with the coupling 112.

The fascia surface is different above and below. The upper fascia surface 128 is a combination of fascia, muscle and fat, more flexible than the lower fascia surface 130 which is peritoneum, a cellophane like substance with little flexibility. The scaffolding serves to align the fascial edges in the anatomic plane and provide a tension free stabilization of tissue critical elements of the abdominal wall. The outer scaffold 106 engages and compresses a combination of subcutaneous fat, fascia and muscle which because of its flexibility is encouraged to move up and around the perforations in the outer scaffold 106. The inner scaffolding 110 directly engages the innermost surface of the abdominal wall, or peritoneal lining 130, creating a bond due to the friction between the abdominal wall and texturing of the inner scaffolding surface, stabilizing the device and indirectly supporting the compressive action of the implantable device.

Figure 3:
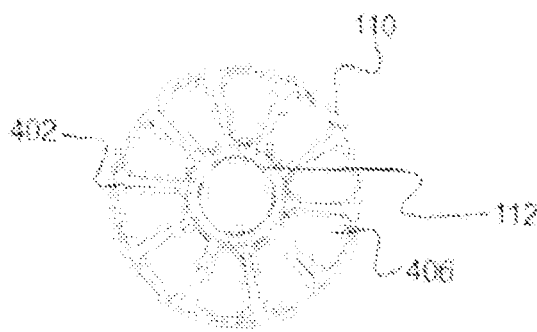
FIG. 3 shows an embodiment of the biodegradable inner scaffolding.

FIG. 3 shows one embodiment of the inner scaffold 110 from a top down view. The inner scaffold is constructed so that it has a set of perforations 406 surrounded by a perimeter 402 with a coupling 112. The coupling 112 enables the inner scaffold to be coupled to the outer scaffold 110. The perforations 406 perform several functions. First, the perforations facilitate the ingrowth of tissue into the wound matrix, promoting faster healing. Perforations also reduce the profile of the device by permitting tissue to position around and through the device. This is expected to minimize patient discomfort of the patient and by further reducing the device profile, minimize the likelihood of feeling a palpable device like this. Finally, the design reduces the biopolymer load and the amount of material required to make the device.

In one or more embodiments, a counter-rotational or frictional control feature can be added to the tissue facing surface of the inner scaffolding 110 which is intended to contact the peritoneum such as small protrusions of a conical shape to prevent the tendency to move during the process of tightening the outer scaffolding 104 onto the coupling 112. In one or more embodiments, this frictional control feature is implemented where the face of the inner scaffolding 110 is textured with a patterned surface to offer frictional control such that, in use, the textured side is placed in direct contact with the fascia and associated layers of the abdominal wall. Its purpose is to hold them in place to facilitate the healing process. In one or more embodiments, the texture is a non-smooth (unpolished) frictional control surface feature to assure that the inner scaffolding 110 remains in position and does not slide or shift laterally during the healing interval.

Figure 4:
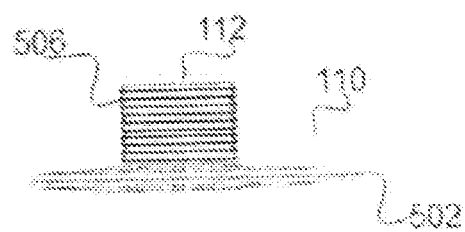
FIG. 4 shows a side view of an embodiment of the biodegradable inner scaffolding.

FIG. 4 shows a side view of the inner scaffold 110. The inner scaffold consists of an inner disk 502 and a coupling 112. In one or more embodiments, the coupling 112 consists of a cylinder 504 with threads inside to enable it to attach to a device for insertion into the trocar defect. The outside of the coupling 506 provides the connection surface to the outer scaffold 106. In one or more embodiments, the coupling provides a surface for a friction coupling such that the outer diameter of the coupling gets slightly larger as it gets closer to the inner disk. In other embodiments it is a snap fit, where the outside surface of the coupling has one or more teeth which mate with the inner surface of the inner ring of the outer scaffold in the same way a cable tie works.

In one or more embodiments, it is understood that the coupling could be a different mechanism, as long as it provides a method for decoupling the inner and outer scaffolding. In one or more embodiments this could be threads on the outside of the coupling and threads on the inner ring of the outer scaffolding. In other embodiments this could be a living hinge snap engagement, where the inner scaffolding has a groove and the outer scaffolding has tines on it such that the tines deflect during installation, returning to undeflected position once they meet the groove. In other embodiments, the coupling could be a keyed circular post where the inner ring of the outer scaffolding is shaped as a keyed circular hole.

Figure 5:
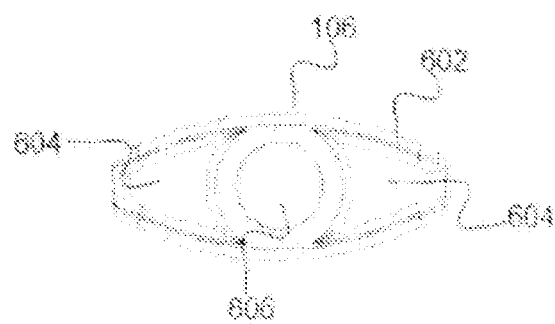
FIG. 5 shows a top view of an embodiment of the biodegradable outer scaffolding.

FIG. 5 shows a top view of the outer scaffold 106. The outer scaffold consists of a perimeter 602, a central ring 606. The central ring 606 has an inner diameter slightly greater than the outer diameter of the inner applicator 114, which enables the outer scaffold to slide over it during the insertion process. The large openings in the outer scaffold 604 act to make the device lower profile as the upper surfaces of the fascia, primarily fat and muscle tissue, protrude through it, somewhat covering it and making it low profile. This reduces the likelihood that the device will be palpable to the patient. The shape of the outer scaffold 106 along with the shape and size differences between the inner scaffold and outer scaffold will encourage the tissue edges to evert, which is further encourages tissue healing to occur.

Figure 6:
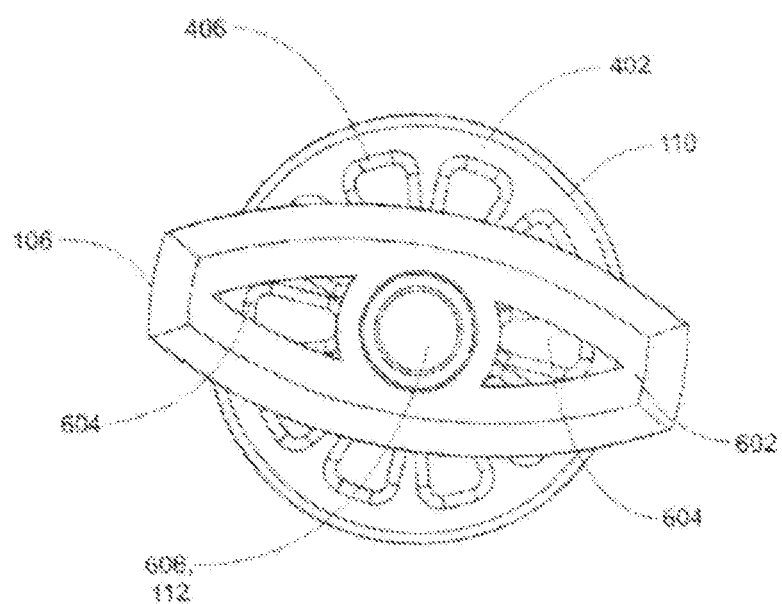
FIG. 6 shows a top down view of the biodegradable scaffolding assembly as it would appear coupled.

FIG. 6 shows a top view of the inner scaffold 110 and outer scaffold 116 as they would be assembled in place. There would also be tissue between the two devices, but this is not shown for clarity. In one or more embodiments, the outer scaffold 116 would be wider as the inner scaffold 110 has to be inserted through the trocar defect and acts as an anchor to hold the scaffolding in place, where the outer scaffold 116 does not have to be inserted through the trocar defect and so can be wider than even the actual defect as long as it fits into the tunnel. The coupling 112 fits through the inner ring of the outer scaffold 606, such that the outer surface of the coupling and the inner surface of the inner ring share a connection means which enables one to insert one into the other easily while making it difficult for the two to unmate without purposely doing so. In one embodiment this is a friction fit, in other embodiments it is a snap fit, but it is recognized that there are many other ways of performing this function.

Because the scaffold encourages the fascia to surround it, the geometry provides less of a need for tension around the trocar defect.

On insertion, the coupling 112 is inside the inner ring of the outer scaffold 106. This aligns the two parts of the scaffolding over the trocar defect, such that even if the outer scaffold 106 is misaligned relative to the direction of the defect, it still provides a large surface for the tissue to penetrate and heal faster because of the circular geometry of the inner scaffold 110.

Figure 7:
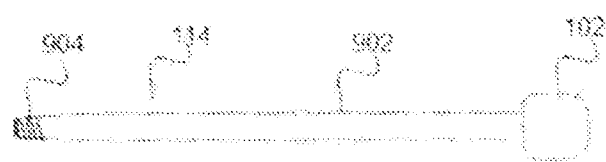
FIG. 7 shows a side view of the inner applicator

FIG. 7 shows a side view of the inner applicator 114. In one or more embodiments, the inner applicator has a handle 102 at the outer end to enable to user to grasp it easier. In other embodiments the inner applicator would have a coupling to enable it to be attached to a robotics controller. The inner applicator has a stem 902 with a threaded inner end 904. The threads are such that they are able to connect to the inner threads of the coupling 112, and the diameter of the stem 902 is such to allow the outer scaffold 106 to slide over the inner diameter of the central ring.

FIG. 8 shows a side view of the outer applicator 104 including an outer cylinder 1002, a dimensional fitting 1004 sized to hold the outer scaffolding 106 in place, and a hole through the center of the cylinder 1006 to allow the inner applicator 114 to slide through. The dimensional fitting 1004 is constructed so that the outline is circular but the outer scaffolding may be elliptical and have a larger major diameter than the diameter of the outer applicator. In one or more embodiments, this is accomplished by having the dimensional fit along the minor diameter of the outer scaffolding, where the outer scaffolding sticks out beyond the outer applicator 104 on either side if its major diameter is larger.

FIG. 9 shows the outer applicator 104 with the outer scaffolding 106 in place. In one or more embodiments, the outer dimensions of the outer scaffolding 106 along its minor diameter are slightly larger than the inner dimensions of the outer applicator wall 1008, so that the outer scaffold is secured in the outer applicator with an interference fit. This means that the outer scaffolding 106 is inserted into the space in the outer applicator 1010 and is held in place with sufficient force that it does not drop out, but with less force than the coupling 112 in combination with the inner scaffolding 110 pulls on it once the inner scaffolding is set beneath the fascia layer. This acts to keep the outer scaffolding 106 stable during the insertion; that is, the outer scaffolding 106 stays aligned with the inner scaffolding 110 such that it can be inserted onto the connector during the insertion process.

General Composition of the Trocar Defect Scaffolding Device

Materials specified for the trocar defect scaffolding device are specific for its intended application and use. The scope of materials that will satisfy the requirements of this application is unusually narrow. This is a direct consequence of the specificity and functional demands characteristic of the intended surgical application.

The intention for the trocar defect scaffolding device is to encourage healing by providing surface area and open space to facilitate tissue growth. This requires a known and finite healing interval of some three to five months. Its purpose fulfilled at the end of this period, making continued presence of the scaffolding a potential liability. To prevent it from becoming a source for irritation once the healing process is completed, the implanted scaffolding should be removed. Consequently, to avoid the need for a second surgical intervention to remove the device, Maurus and Kaeding (Maurus, P. B. and Kaeding, C. C., "Bioabsorbable Implant Material Review", *Oper. Tech. Sports Med* 12, 158-160, 2004) found it was a primary requirement for a wound closure device is that it is biodegradable. This means that the materials will degrade or disintegrate, being absorbed in the surrounding tissue in the environment of the human body, after a definite, predictable and desired period of time. One advantage of such materials over non-degradable or essentially stable materials is that after the interval for which they are applied (i.e. healing time) has elapsed, they are no longer a contributing asset and do not need subsequent surgical intervention for removal, as would be required for materials more stable and permanent. This is most significant as it minimizes risks associated with repeat surgeries and the additional trauma associated with these procedures.

A disadvantage of these types of materials is that their biodegradable characteristic makes them susceptible to degradation under normal ambient conditions. There is usually sufficient moisture or humidity in the atmosphere to initiate their degradation even upon relatively brief exposure. This means that precautions must be taken throughout their processing and fabrication into useful forms, and in their storage and handling, to avoid moisture absorption. This is not a serious limitation as many materials require handling in controlled atmosphere chambers and sealed packaging; but it is essential that such precautions are observed. Middleton and Tipton (Middleton, J. and Tipton A. "Synthetic Biodegradable Polymers As Medical Devices" *Medical Plastics and Biomaterials Magazine*, March 1998) found that this characteristic also dictates that their sterilization before surgical use cannot be done using autoclaves, but alternative approaches must be employed (e.g. exposure to atmospheres of ethylene oxide or gamma radiation with cobalt 60).

While biodegradability is an essential material characteristic for the wound closure device, the intended application is such that a further requirement is that the material is formulated and manufactured with sufficient compositional and process control to provide a precisely predictable and reliable degree of biodegradability. The period of biodegradability corresponds to the healing interval for the trocar defect in the fascia layer, which is typically three to five months.

In these materials, simple chemical hydrolysis of the hydrolytically unstable backbone of the polymer is the prevailing mechanism for its degradation. As discussed in Middleton and Tipton (Middleton, J. and Tipton A referenced previously), this type of degradation when the rate at which water penetrates the material exceeds that at which the polymer is converted into water-soluble materials is known as bulk erosion.

Biodegradable polymers may be either natural or synthetic. In general, synthetic polymers offer more advantages than natural materials in that their compositions can be more readily finely-tuned to provide a wider range of properties and better lot-to-lot uniformity and, accordingly, offer more general reliability and predictability and are the preferred source.

Synthetic absorbable materials have been fabricated primarily from three polymers: polyglycolic acid (PGA), polylactic acid (PLA) and polydioxanone (PDS). These are alpha polyesters or poly (alpha-hydroxy) acids. The dominant ones are PLA and PGA and have been studied for several decades. Gilding and Reed (Gilding, D. K and Reed A. M., "Biodegradable Polymers for Use in Surgery" *Polymer* 20, 1459-1464) discussed how each of these materials has distinctive, unique properties. One of the key advantages of these polymers is that they facilitate the growth of blood vessels and cells in the polymer matrix as it degrades, so that the polymer is slowly replaced by living tissue as the polymer degrades ("Plastic That Comes Alive: Biodegradable plastic scaffolds support living cells in three dimensional matrices so they can grow together into tissues and even whole organs" by Cat Faber Strange Horizons http://www.strangehorizons.com/2001/20010305/plastic.shtml)

In recent years, researchers have found it desirable for obtaining specific desirable properties to prepare blends of these two dominant types, resulting in a highly useful form, or co-polymer, designated as PLGA or poly (lactic-co-glycolic acid). Asete and Sabilov (Asete, C. E. and Sabilov C. M., "Synthesis and Characterization of PLGA Nanoparticles", *Journal of Biomaterials Science—Polymer Edition* 17(3) 247-289 (2006)) discuss how this form is currently used in a host of FDA-approved therapeutic devices owing to its biodegradability and biocompatibility.

In one or more embodiments, the biodegradable scaffold may be made of biodegradable material of different stability (i.e. half-life). While it is important for the material that is in direct contact with the fascia or lending support to that (the inner scaffolding 110, and outer scaffolding 106) needs to stay in place for a few months, while the rest of the implantable structure can degrade significantly in a matter of weeks without affecting the performance of the payload. In one or more embodiments, the coupling 112 would degrade sooner than the inner scaffolding 110 and outer scaffolding 106, so that the ends of the defect are allowed to grow together while protecting the surface of the defect.

Description of Use of One or More Embodiments of the Invention

One or more embodiments of the use of this invention are described herein. In one or more embodiments, the outer applicator 104 is coupled to the outer scaffold 106 first, then the inner applicator 114 is inserted through the outer applicator 104 and then coupled to the inner scaffold 110 through the coupling 112. The outer scaffold 106 is fitted over the coupling 112. The combination of the scaffolds, connector and applicators creates what we will refer to as the applicator assembly.

As shown in FIG. 1, the applicator assembly is inserted into the trocar tunnel surrounded by the skin 122, subcutaneous fat 120 with the outer scaffold 106 connected to the outer applicator 104 and the inner applicator 114 attached to the inner scaffold 110. The user is able to manipulate the assembly using the handle 102. At this point, the inner scaffold 110 has not reached the trocar defect 124 or surrounding fascia tissue 126.

Prior to insertion, the device is assembled in one or more embodiments as follows. The inner applicator 114 is inserted into the central hole of the outer applicator 1006 such that the screw end is closest to the inner end of the outer applicator 1004. Either before inserting the inner applicator into the outer applicator or after, the outer scaffolding 106 is attached to the inner end of the outer applicator by inserting it into the dimensional fit 1004. If the inner applicator 114 is in place, this is accomplished by sliding the outer scaffolding over the end of the inner applicator 114 towards the dimensional fit of the outer applicator 1004. Finally, screw the coupling 112 onto the threads of the inner applicator 904.

Figure 10:
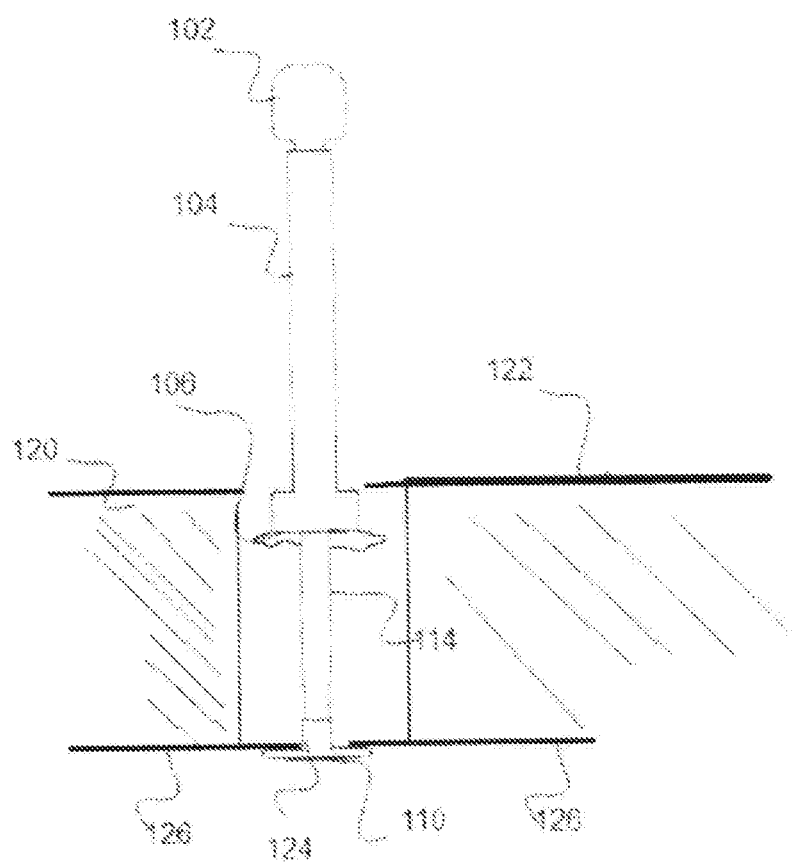
FIG. 10 shows an embodiment of the insertion of the inner scaffolding below the trocar defect.

As shown in FIG. 10, the inner scaffold 110 is pushed through the trocar defect 1206. Once the inner scaffold is pushed through the trocar defect 124, the user exerts a slight upward pressure on the handle 102 of the inner applicator 114 to keep the inner scaffold 110 securely against the lower fascia surface 126 and under the trocar defect 124.

Figure 11:
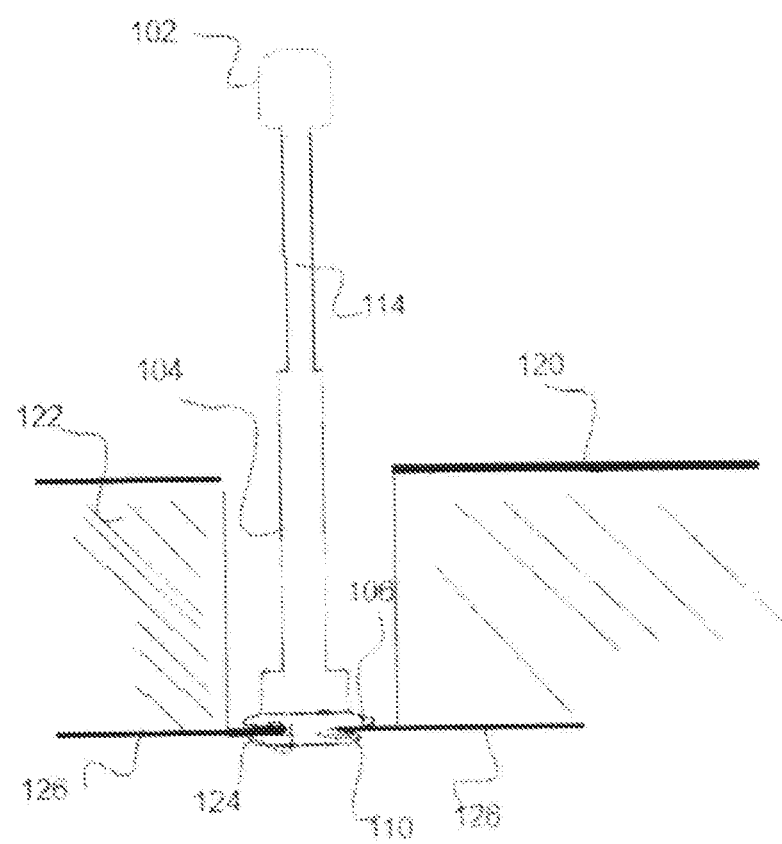
FIG. 11 shows an embodiment of the connection of the inner scaffolding and outer scaffolding around the trocar defect

In one or more embodiments where the outer scaffold 106 is made to slide over the connector the user will also exert a downward pressure on the tube of the outer applicator 1002 to move the outer scaffold 106 over the coupling 112 toward the inner scaffold until there is a positive force pushing back. When the outer scaffold 106 is over the coupling 112, the coupling will pass through the inner center hole in the outer connector, stabilizing it while the insertion is completing. In other embodiments, the tube is rotated where the outer scaffold has a threaded interface with the connector. At this point, the device is set in place, as shown in FIG. 11.

Figure 12:
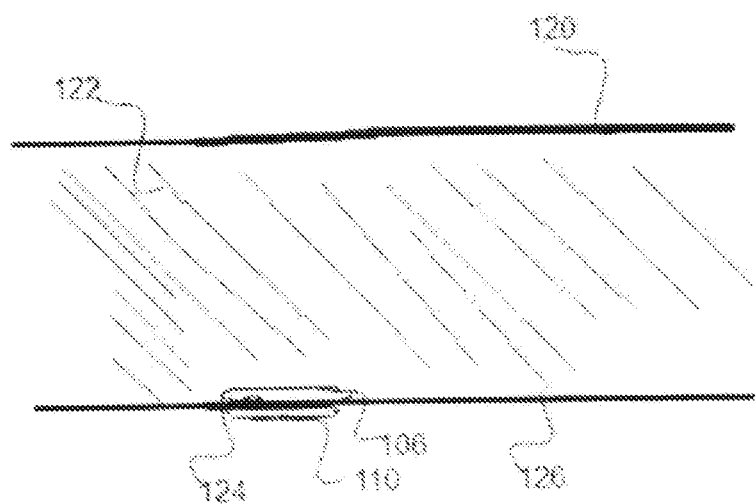
FIG. 12 shows an embodiment of the healing process with the applicator removed and the tissue healing around the scaffolding assembly

Once the device is in place, the outer applicator 104 can be decoupled from the outer scaffold 106 and the inner applicator 114 is decoupled from the coupling 112. The user is then free to close the outer wound 122. At this point the skin is closed and over a period of time the skin 122 and subcutaneous fat 120 heal and grow into the former trocar tunnel. The trocar defect also heals and you just have the fascia 126. The result of this is shown in FIG. 12.

Figure 13:
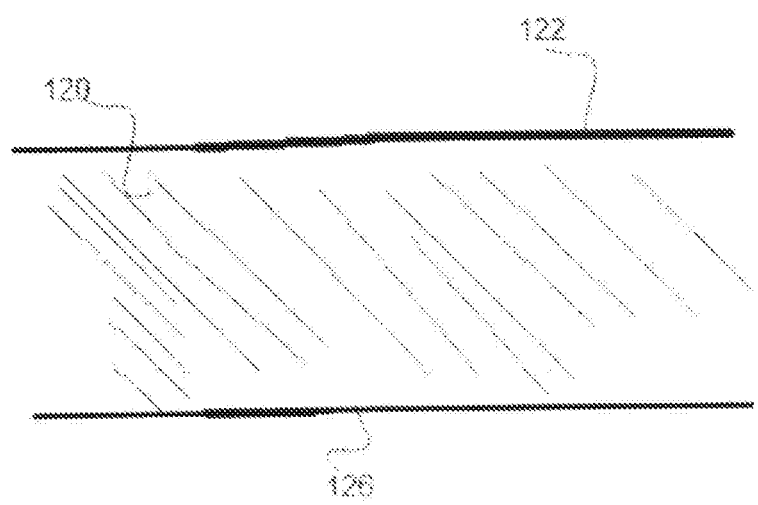
FIG. 13 shows the end of the healing process, with the tissue fully healed and the biodegradable scaffolding assembly dissolved.

Over the next few months, the wound edges will grow into each other. In one or more embodiments, the fascia layers are encouraged to grow into the device itself. Over time, the device degrades and eventually dissolves into the body to be excreted without any known side effects, leaving behind a healed fascia 126 under the layers of skin 122 and subcutaneous fat 120 as shown in FIG. 13.

What is claimed is:

1. A method for promoting the healing of a trocar defect without effecting complete wound closure, the method comprising:
   providing an outer scaffolding means for promoting healing by encouraging the growth of tissue around the trocar defect, said outer scaffolding means at least large enough to fit across a portion but not all of the trocar defect;
   providing an inner stabilizing means for maintaining the location of the outer scaffolding means without undue compression and for promoting healing by encouraging the growth of tissue around the trocar defect, said inner stabilizing means large enough to fit across a portion but not all of the trocar defect;
   providing a coupling means for connecting the outer scaffolding means to the inner stabilizing means;
   providing an inserting means for inserting and placing the inner stabilizing means into the trocar defect;
   providing a compressing means for detachably connecting the outer scaffolding means to the coupling means;
   providing a connecting means for slidably connecting the outer scaffolding means to the inserting means;
   detachably connecting the inner stabilizing means to the inserting means;
   detachably connecting the outer scaffolding means to the compressing means;
   detachably connecting the inserting means to the compressing means;
   inserting the inserting means into the trocar tunnel with the compressing means attached;
   pushing the inner stabilizing means through the trocar defect using the inserting means;
   pushing back on the inserting means so that the inner stabilizing means is up against the inner wall of the trocar defect;
   pushing on the compressing means while keeping the inserting means in place until there is resistance to further compression of the tissue, such that the edges of the trocar defect are aliened;
   disconnecting the inserting means from the inner stabilizing means;
   disconnecting the compressing means from the outer scaffolding means;
   removing the inserting means and compressing means from the trocar tunnel;
   maintaining the position of the outer scaffolding means over the trocar defect using the inner stabilizing means; and
   enabling the tissue associated with the trocar defect to heal by using the outer scaffolding means.

2. The method in claim 1, the inner stabilizing means having a first base diameter, the inner stabilizing means having a tissue facing surface, the tissue facing surface having one or more perforations around a central ring.

3. The method in claim 2, the outer scaffolding means comprising:
   a tissue facing surface, an inner ring and a perimeter, the outer scaffolding means having a multiplicity of perforations between the inner ring and the perimeter.

4. The method in claim 3, the coupling means connected to the tissue facing surface of the inner stabilizing means, the coupling means having an outer diameter, where the outer diameter of the coupling means is less than the inner diameter of the inner ring and wherein the length of the coupling means is sufficient to connect the inner stabilizing means to the outer scaffolding means, while allowing enough space between the inner stabilizing means and the outer scaffolding means to maintain a predefined gap substantially equal to the thickness of the fascia.

5. The method in claim 1, the inserting means having an outer diameter, an outer end, an inner end, and threads on the outer surface of the inner end.

6. The method in claim 1, the compressing means having an outer diameter substantially less than the trocar tunnel diameter but substantially larger than the outer diameter of the inserting means, the compressing means having a cylindrical shape with an inner end and an outer end, the outer end having a compressing means first central hole, the inner end having a means for the outer scaffolding means to be set and a compressing means second central hole, wherein the compressing means first central hole and compressing means second central hole are large enough for the inserting means to pass through.

7. The method in claim 1, wherein the compressing means comprises a dimensional fit and a connecting means second central hole, where the dimensional fit is configured to detachably connect to the outer scaffolding means, while allowing the inserting means to pass through into the connecting means second central hole, and allowing the inner stabilizing means to be set into the outer scaffolding means.

* * * * *